(12) United States Patent
Yang et al.

(10) Patent No.: US 10,767,428 B2
(45) Date of Patent: Sep. 8, 2020

(54) DEVICE AND METHOD FOR SIMULATING FORMATION RESPIRATION EFFECT

(71) Applicant: China University of Petroleum—Beijing, Beijing OT (CN)

(72) Inventors: Jin Yang, Beijing (CN); Qishuai Yin, Beijing (CN); Shanshan Shi, Beijing (CN)

(73) Assignee: CHINA UNIVERSITY OF PETROLEUM—BEIJING, Bejing (CN)

( * ) Notice: Subject to any disclaimer, the term of this patent is extended or adjusted under 35 U.S.C. 154(b) by 0 days.

(21) Appl. No.: 16/514,965

(22) Filed: Jul. 17, 2019

(65) Prior Publication Data

US 2020/0217156 A1    Jul. 9, 2020

(30) Foreign Application Priority Data

Jan. 8, 2019    (CN) .......................... 2019 1 0016340

(51) Int. Cl.
*E21B 21/08*      (2006.01)
*E21B 47/00*      (2012.01)
*E21B 43/12*      (2006.01)

(52) U.S. Cl.
CPC ............ *E21B 21/08* (2013.01); *E21B 43/126* (2013.01); *E21B 47/00* (2013.01)

(58) Field of Classification Search
CPC ........... E21B 21/08; E21B 47/00; E21B 43/25
See application file for complete search history.

(56) References Cited

U.S. PATENT DOCUMENTS

| 4,538,452 A | * | 9/1985 | Hrvojic | .............. G01N 15/0618 |
| | | | | 73/290 V |
| 4,848,145 A | * | 7/1989 | Blaschke | .............. E21B 43/267 |
| | | | | 73/152.55 |

(Continued)

FOREIGN PATENT DOCUMENTS

| CN | 1536341 | 10/2004 |
| CN | 102979505 | 3/2013 |

(Continued)

OTHER PUBLICATIONS

PCT Specialized Search Report prepared by the China Patent Information Center dated Mar. 29, 2019.

(Continued)

*Primary Examiner* — John Fitzgerald
(74) *Attorney, Agent, or Firm* — Loza & Loza, LLP; Michael F. Fedrick

(57) ABSTRACT

A formation respiration effect simulation device having an outer cylinder in which an artificial formation is disposed, the artificial formation having an artificial borehole, with an outer portion of the artificial formation being wrapped by an air cushion and a lower annular space being formed between the air cushion and the outer cylinder. An inner cylinder is hermetically disposed above the artificial formation, an upper annular space being formed between the inner cylinder and the outer cylinder, with the upper annular space communicating with the lower annular space. A liquid injection pipe is pierced in the inner cylinder and extends into the artificial borehole. A monitoring mechanism having a liquid level monitor is included to monitor a liquid level height of a fluid medium in the lower annular space, and a pressure sensor is disposed at a lower end surface of the inner cylinder and located within the artificial borehole.

10 Claims, 2 Drawing Sheets

(56) References Cited

U.S. PATENT DOCUMENTS

| | | | | |
|---|---|---|---|---|
| 4,982,604 | A * | 1/1991 | Davis | G01N 33/241 |
| | | | | 324/376 |
| 5,299,453 | A * | 4/1994 | Sprunt | G01N 15/0893 |
| | | | | 436/31 |
| 10,095,819 | B2 * | 10/2018 | Li | E21B 43/16 |
| 2003/0225521 | A1 * | 12/2003 | Panga | E21B 43/25 |
| | | | | 702/6 |
| 2004/0220742 | A1 * | 11/2004 | Mese | E21B 44/00 |
| | | | | 702/11 |
| 2007/0271039 | A1 | 11/2007 | Ella et al. | |
| 2016/0102541 | A1 | 4/2016 | Kronenberger et al. | |
| 2016/0357888 | A1 * | 12/2016 | Li | E21B 43/34 |
| 2020/0056477 | A1 * | 2/2020 | Yang | E21B 49/001 |

FOREIGN PATENT DOCUMENTS

| | | |
|---|---|---|
| CN | 103257079 | 8/2013 |
| CN | 104863533 | 8/2015 |
| CN | 105735981 | 7/2016 |
| CN | 107869345 | 4/2018 |
| CN | 108915595 | 11/2018 |

OTHER PUBLICATIONS

Numerical stimulation of formation tester fluid identification module fluid barrel, Petrochemical Industry Application, vol. 31, No. 2, pp. 92-94, 104 (2012).

Discussion on Identifying and Handling of Formation Ballooning, Offshore oil, vol. 34, No. 1, pp. 72-76, Mar. 2014.

Research of real-time monitoring system for offshore well blowout, Master's Thesis of Gang Wang, Xi'an Shiyou University, May 31, 2017.

Study on the Respiration Effect Mechanism of Gas Flow in Deep Coal Seam, Doctoral Thesis of Wei Zhang, School of Electrical and Power Engineering, China University of Mining, May 2017.

Search Report prepared by the China Patent Information Center dated Dec. 30, 2018.

* cited by examiner

DEVICE AND METHOD FOR SIMULATING FORMATION RESPIRATION EFFECT

RELATED APPLICATION

This application claims priority under 35 U.S.C. § 119 to Chinese Patent Application No. 201910016340.6, filed Jan. 8, 2019, the disclosures of which are incorporated herein by reference.

TECHNICAL FIELD

The invention relates to the technical field of oil drilling and completion, and in particular to a device and a method for simulating a formation respiration effect.

BACKGROUND ART

With the increase of exploration and development of oil and gas resources and great improvement on the oil and gas exploration and development technology and equipment capability, the field of oil and gas development gradually shifts from land to ocean, from shallow sea water to deep sea water, from a normal-temperature and normal-pressure formation to a high-temperature and high-pressure formation or to even an ultra-high temperature and ultra-high pressure formation, and the operation of oil and gas exploration and development is also becoming more and more difficult.

In the drilling and completion operation of the high-temperature and high-pressure formation or even the ultra-high temperature and ultra-high pressure formation, because a pore pressure of a target interval formation is high and the pore pressure is close to a fracture pressure, during drilling and completion operation a safe drilling fluid density window is narrow or even there is no safe window, as a result, in order to balance the pore pressure of the formation during operation, mud with a high specific gravity has to be used, and when fluid column pressure of the mud with a high specific gravity within a well is higher than or approaches a formation leakage pressure, the mud in the well enters into the interior of the formation along the formation fracture under the action of pressure difference, higher liquid column pressure will also cause a primary fracture of the formation to open and a new fracture is formed. However, when the mud in the well stops circulating or the pressure of the fluid column in the well decreases due to other reasons, the primary fracture and newly formed fractures of the formation will close, and the high specific gravity mud filtrate that previously entered the interior of the formation due to the action of pressure difference may return to the interior of the borehole.

The phenomenon that mud enters the formation and then returns to the interior of the borehole under the action of pressure difference is a formation respiration effect. When the respiration effect occurs in the drilling process especially in the high-temperature and high-pressure formation, it is very difficult to accurately recognize the actual situation of downhole due to the complexity of the downhole situation, the process "inhalation" of the respiration effect is often mistaken as leakage of the mud, and thus the mud density is erroneously reduced to induce underground overflow; and the "exhalation" process of the respiration effect is mistaken as that there is an overflow underground, thus a well killing job is performed wrongly, which causes the formation fracture to be opened further, and a large amount of mud enters into the interior of the formation, resulting in a large amount of human, material and financial loss.

SUMMARY OF THE INVENTION

The object of the present invention is to provide a device and a method for simulating a formation respiration effect, which can carry out indoor simulation of the formation respiration effect, find out characteristics of the formation respiration effect in different operation conditions under different formation conditions, to provide a theoretical guidance for on-site drilling and completion operations.

The above object of the present invention can be achieved by adopting the following technical solutions:

The present invention provides a device for simulating a formation respiration effect, comprising:

an outer cylinder in which an artificial formation is disposed, the artificial formation having an artificial borehole, an outer portion of the artificial formation being wrapped by an air cushion, and a lower annular space being formed between the air cushion and the outer cylinder;

an inner cylinder which is hermetically disposed above the artificial formation, an upper annular space being formed between the inner cylinder and the outer cylinder, the upper annular space communicating with the lower annular space; a liquid injection pipe being pierced in the inner cylinder, and the liquid injection pipe being able to extend into the artificial borehole; and a monitoring mechanism having a liquid level monitor capable of monitoring a liquid level height of a fluid medium in the lower annular space, and a pressure sensor disposed at a lower end surface of the inner cylinder and located within the artificial borehole.

The present invention also provides a simulation method of a formation respiration effect simulation device as described above, the simulation method comprising the steps of:

a step S1 of injecting a fluid medium into the lower annular space of the formation respiration effect simulation device, and recording an initial liquid level height in the lower annular space;

a step S2 of injecting the fluid medium into the artificial borehole of the artificial formation through the liquid injection pipe of the formation respiration effect simulation device, and monitoring pressure data in the artificial hole by the pressure sensor, until a pressure value monitored by the pressure sensor reaches an initial set pressure value;

a step S3 of maintaining the initial set pressure value for a set time period, and monitoring a liquid level height of the fluid medium in the lower annular space by the liquid level monitor;
and a step S4 of changing an injection pressure of the fluid medium flowing into the liquid injection pipe and maintaining the injection pressure for a certain period of time, and monitoring the current liquid level height of the fluid medium in the lower annular space in real time by the liquid level monitor.

The characteristics and advantages of the device and the method for simulating a formation respiration effect according to the present invention are as follows: the invention can truly simulate the actual working conditions of the field and carry out the indoor simulation of the formation respiration effect; and can simulate the process that fluid within the artificial borehole enters the artificial formation under different pressure and the quantity of that fluid entering the artificial formation; and can further stimulate the process that the fluid medium that enters the artificial formation returns into the artificial borehole and the quantity of the returned fluid medium; the invention can solve the problem that the formation respiration effect is difficult to recognize during on-site operation, which leads to complex downhole accidents caused by blind well control operation. The present invention can simulate the process of formation respiration effect under different formation conditions and different operation conditions by setting different experimental conditions, and explore a solution to reduce the disadvantage of formation respiration effect on recognition of drilling conditions.

DETAILED DESCRIPTION OF THE PREFERRED EMBODIMENTS

Hereinafter the technical solution in the embodiments of the present invention will be described clearly and integrally in combination with the accompanying drawings in the embodiments of the present invention, and obviously the described embodiments are merely part of the embodiments, not all of the embodiments. Based on the embodiments of the present invention, all other embodiments that are obtained by persons skilled in the art without making creative efforts fall within the protection scope of the present invention.

Embodiment 1

Figure 1:
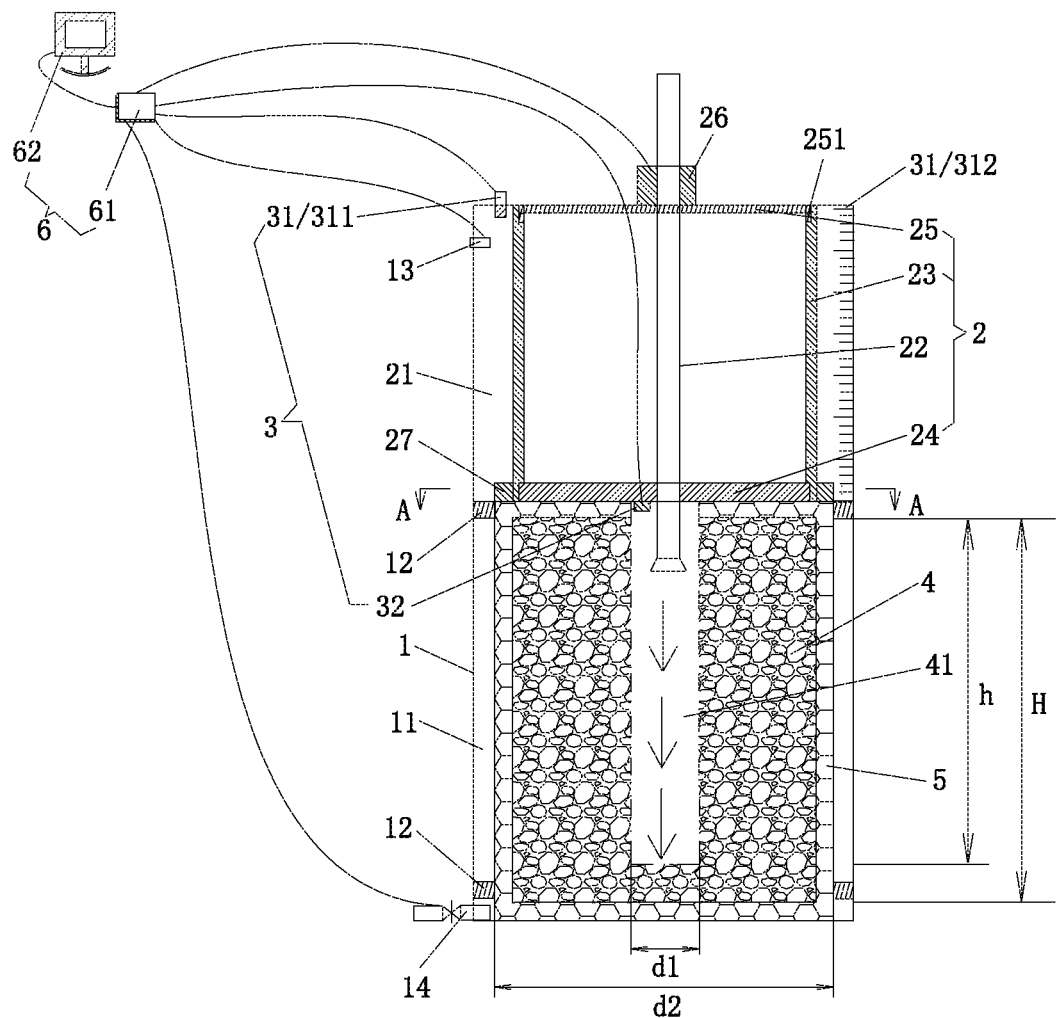
FIG. 1 is a structural schematic of a formation respiration effect simulation device according to the present invention.
Figure 2:
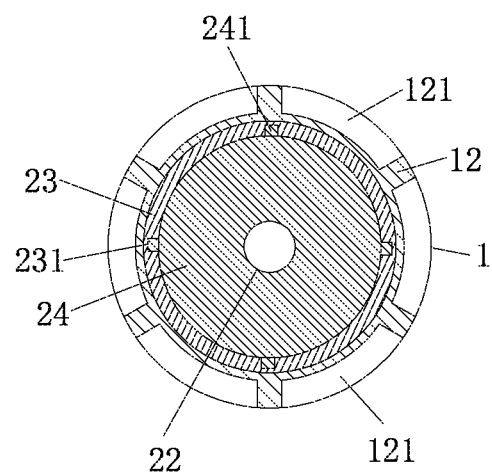
FIG. 2 is a cross-sectional view taken along the line A-A of FIG. 1.
Figure 3:
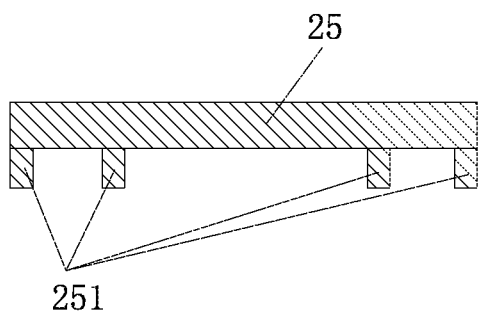
FIG. 3 is a structural schematic of an upper cover of the formation respiration effect simulation device according to the present invention.

As shown in FIGS. 1 to 3, the present invention provides a formation respiration effect simulation device, comprising an outer cylinder 1, an inner cylinder 2 and a monitoring mechanism 3, wherein an artificial formation 4 is disposed within the outer cylinder 1, the artificial formation 4 has an artificial borehole 41, an outer portion of the artificial formation 4 is wrapped by an air cushion 5, and a lower annular space 11 is formed between the air cushion 5 and the outer cylinder 1; the inner cylinder 2 is hermetically disposed above the artificial formation 4, an upper annular space 21 is formed between the inner cylinder 2 and the outer cylinder 1, the upper annular space 21 communicates with the lower annular space 11; a liquid injection pipe 22 is pierced in the inner cylinder 2, and the liquid injection pipe 22 is able to extend into the artificial borehole 41; the monitoring mechanism 3 has a liquid level monitor 31 capable of monitoring a liquid level height of a fluid medium in the lower annular space 11, and a pressure sensor 32 disposed at a lower end surface of the inner cylinder 2 and located within the artificial borehole 41.

Specifically, the outer cylinder 1 is substantially cylindrical, and in this embodiment, the outer cylinder 1 may be a transparent cylinder, such as a cylinder made of transparent high-strength glass or a high-strength plastic material, an outer portion of the outer cylinder 1 is wrapped by a metal protective layer, to protect the outer cylinder 1 from damage and meanwhile to be able to observe conditions inside the outer cylinder 1.

The artificial formation 4 is placed at the bottom inside the outer cylinder 1, which is artificially simulated cylindrical formation, can simulate artificial formations of different fracture development degrees and fracture shapes according to the needs of experiment. An artificial borehole 41 is provided from an upper end face of the artificial formation 4 into the artificial formation 4, the artificial borehole 41 is arranged along axis of the artificial formation 4 and is an impenetrable borehole, so as to stimulate the formation respiration effect. In the present embodiment, an outer diameter of the artificial formation 4 is smaller than an inner diameter of the outer cylinder 1, and a diameter d1 of the artificial borehole 41 is slightly larger than an outer diameter of the liquid injection pipe 22 so that the liquid injection pipe 22 can protrude therein. The fluid medium injected into the artificial borehole 41 of the artificial formation 4 by the liquid injection pipe 22 enters the artificial formation 4, such that the artificial formation 4 is deformed or the fluid medium completely penetrates the artificial formation 4.

The air cushion 5 is wrapped outside the artificial formation 4, that is, the air cushion 5 is provided at the bottom, the peripheral side wall and the top of the cylindrical artificial formation 4, the air cushion 5 is arranged tightly close to the bottom wall, the peripheral side wall and the top wall of the artificial formation 4, an outer diameter d2 of the air cushion 5 is smaller than an inner diameter of the outer cylinder 1 and is slightly larger than an outer diameter of the artificial formation 4, and a lower annular space 11 is formed between the air cushion 5 and the outer cylinder 1. When the artificial formation 4 is deformed, the air cushion 5 may be deformed, and volume of the lower annular space 11 between the air cushion 5 and the outer cylinder 1 may be changed. That is, when the fluid medium within the artificial borehole 41 enters the artificial formation 4, the volume of the artificial formation 4 increases to cause radial expansion of the air cushion 5, at which time the volume of the lower annular space 11 decreases, the liquid level height of the fluid medium in the lower annular space 11 rises. When the pressure of the fluid medium in the artificial borehole 41 drops, the fluid medium entering the artificial formation 4 is returned into the artificial borehole 41 of the artificial formation 4, the volume of the artificial formation 4 is restored to some extent, and the volume of the lower annular space 11 increases with this, and the liquid level height of the lower annular space 11 decreases.

In an embodiment of the invention, the lower annular space 11 is provided with at least two support rings 12, which sleeve on an outer side of the air cushion 5 and are spaced apart in an axial direction of the outer cylinder 1, and each support ring 12 is provided with a plurality of flow grooves 121 at intervals in a circumferential direction thereof. The support rings 12 serve the purpose of fixing the artificial formation 4 and the air cushion 5 within the outer cylinder 1, and can ensure that the artificial formation 4 and the air cushion 5 do not slide relative to the outer cylinder 1.

As shown in FIG. 2, the plurality of flow grooves 121 provided on the support rings 12 enable the fluid medium in the lower annular space 11 to flow into the upper annular space 21. In this embodiment, an upper end side wall and a lower end side wall of the air cushion 5 are respectively sleeved with a support ring 12, and six flow grooves 121 are provided at equal intervals in the circumferential direction of each support ring 12.

The inner cylinder 2 is hermetically disposed on the upper end face of the artificial formation 4. In this embodiment, the inner cylinder 2 has an inner cylinder body 23, a lower end of the inner cylinder body 23 is hermetically connected with an inner sealing cover 24, and an upper end of the inner cylinder body 23 is hermetically connected with an upper cover 25, the liquid injection pipe 22 passes through the upper cover 25 and the inner sealing cover 24, and the liquid injection pipe 22 is in sealed connection with the inner sealing cover 24.

Specifically, a plurality of axial through grooves 231 are provided at intervals in the circumferential direction on an inner wall of the inner cylinder body 23, and a plurality of sliding blocks 241 are provided at intervals in the circumferential direction on an outer wall of the inner sealing cover 24, the sliding blocks 241 are embedded in the axial through grooves 231 in a sealed sliding manner, so that the inner sealing cover 13 can be sealingly connected to the inner cylinder body 23 along the axial through groove 231. In this embodiment, as shown in FIG. 2, four axial through grooves 231 are provided at equal intervals in the circumferential direction on an inner wall of the inner cylinder body 23, four sliding blocks 241 are provided at equal intervals in the circumferential direction on an outer wall of the inner sealing cover 24, and the four sliding blocks 241 can be embedded in the four axial through grooves 231; of course, in other embodiments, the number of the axial through grooves 231 of the inner cylinder body 23 and the sliding blocks 241 of the inner sealing cover 24 may be three, five, or more, and is not limited herein.

As shown in FIG. 3, a plurality of insertion blocks 251 are provided at intervals in the circumferential direction on a lower end face of an upper cover 25, and in a state that the upper cover 25 is placed on the upper end of the inner cylinder body 23, these insertion blocks 251 can be clamped in the axial through grooves 231, such that the upper cover 25 can be stably connected onto the inner cylinder body 23.

The liquid injection pipe 22 is substantially cylindrical and is pierced in the upper cover 25 and the inner sealing cover 24. One end of the liquid injection pipe 22 is connected to an external water pump, and the other end of the liquid injection pipe 22 can extend into the artificial borehole 41 of the artificial formation 4. The water pump is started, to achieve the purpose of injecting water into the artificial borehole 41 of the artificial formation 4 by means of the liquid injection pipe 22. In this embodiment, the liquid injection pipe 22 is connected to the inner sealing cover 24 by seal welding, and the fluid medium injected into the artificial borehole 41 of the artificial formation 4 through the liquid injection pipe 22 is a high-pressure fluid, the pressure of the high-pressure fluid is higher than a minimum pressure that allows the fluid medium to enter the interior of the artificial formation 4 (typically associated with the artificial formation 4), or the pressure of the high-pressure fluid may be taken as a pressure value of mud fluid column at the depth of the simulated formation, for example, if the depth of the simulated formation is H, the pressure of the high-pressure fluid is about: density of the high-pressure fluid ×H.

In this embodiment, a driving mechanism 26, such as an elevator or a screw mechanism and etc., is mounted on the upper cover 25, and the liquid injection pipe 22 and the inner sealing cover 24 can be lifted or lowered under the action of the driving mechanism 26, such that the liquid injection pipe 22 and the inner sealing cover 24 are moved in the axial direction of the inner cylinder body 23. The inner sealing cover 24 can be lowered down against the air cushion 5 above the artificial formation 4. In the invention, a contact part of the inner cylinder 2 and the air cushion 5 above the artificial formation 4 is sealed, for example, the outer wall of the liquid injection pipe 22 at a lower side of the inner sealing cover 24 is sleeved with a sealing ring and a gasket. An outer diameter of the gasket is the same as an outer diameter of the sealing ring, and is larger than a diameter of the artificial borehole 41 of the artificial formation 4. The sealing ring and the gasket are tightly fixed on the outer wall of the liquid injection pipe 22 and abut the lower end face of the inner sealing cover 24. When the inner sealing cover 24 is pressed down, the sealing ring and the gasket can be pressed against the air cushion 5 on the upper end face of the artificial formation 4 to prevent leakage of the fluid medium via a position where the inner sealing cover 23 contacts the air cushion 5, and leakage of the high-pressure fluid within the artificial borehole 41 of the subsequent artificial formation 4 is avoided.

The diameter of the inner cylinder body 23 is the same as the outer diameter of the artificial formation 4. In this embodiment, the outer wall of the lower end of the inner cylinder 2 is provided with a ring boss 27 having an outer diameter that is the same as or slightly larger than an outer diameter d2 of the air cushion 5. The ring boss 27 is used to fix a part of the air cushion 5 wrapped around the upper end face of the artificial formation 4, and the outer diameter of the ring boss 27 is smaller than the inner diameter of the outer cylinder 1.

The monitoring mechanism 3 has a liquid level monitor 31 and a pressure sensor 32. The liquid level monitor 31 is used to monitor a liquid level height of the fluid medium within the lower annular space 11 in real time. In a feasible embodiment, the liquid level monitor 31 is an infrared ranging sensor 311 which is disposed at an upper end of the outer cylinder 1; or in another feasible embodiment, the liquid level monitor 31 is a graduation line 312 provided on the upper outer wall of the outer cylinder 1.

The pressure sensor 32 is mounted at the lower end of the inner cylinder 2 and is located within the artificial borehole 41 of the artificial formation 4, and the pressure sensor 32 is used for monitoring the pressure of the fluid medium in the artificial borehole 41 of the artificial formation 4.

Further, a liquid injection valve 13 is provided at the upper end of the outer cylinder 1, and a liquid discharge valve 14 is provided at the lower end of the outer cylinder 1. The liquid injection valve 13 communicates with the upper annular space 21, and the liquid discharge valve 14 communicates with the lower annular space 11. The fluid medium can be injected into the lower annular space 11 through the liquid injection valve 13, and the fluid medium in the lower annular space 11 can be discharged through the liquid discharge valve 14.

In an embodiment of the invention, the formation respiration effect simulation device further comprises a control system 6 comprising a data collection mechanism 61 and a controller 62 that are electrically connected. The data collection mechanism 61 is used to collect the liquid level height of the fluid medium in the lower annular space 11 and pressure data in the artificial borehole 41 of the artificial formation 4. The controller 62 controls opening and closing of the liquid injection valve 13 and the liquid discharge valve 14 through the collected data, and controls the start-stop and power of the driving mechanism 26 and the water pump (not shown).

The experimental steps of the formation respiration effect simulation device are as follows:

a step S1 of drilling the machined artificial formation 4 stimulating different fracture development degrees in the axial direction to form an artificial borehole 41, a depth h of the artificial borehole 41 being smaller than the height H of the artificial formation 4;

a step S2 of sleeving the support ring 12 on the air cushion 5 outside the artificial formation 4, such that the air cushion 5 can be completely and tightly wrapped around the side surface, the top end face and the bottom end face of the artificial formation 4;

a step S3 of suspending the artificial formation 4 sleeved with the air cushion 5 in the inside of the outer cylinder 1, and seating the artificial formation 4 at a central position within the outer cylinder 1;

a step S4 of seating the inner cylinder 2 on the air cushion 5 on the upper end face of the artificial formation 4, mounting the upper cover 25 of the inner cylinder 2, lowering the inner sealing cover 23 of the inner cylinder 2 to the air cushion 5 that presses against the upper end face of artificial formation 4, and meanwhile sealing the inner cylinder 2 and a contact part between the inner sealing cover 23 and the artificial formation 4, to prevent later overflowing of the high-pressure fluid medium inside the artificial borehole 41;

a step S5 of injecting the fluid medium into the lower annular space 11 between the outer cylinder 1 and the air cushion 5 through the liquid injection valve 13, in this embodiment, the fluid medium may be water or other non-corrosive, non-toxic fluid such as oil, drilling fluid or air or the like, until a liquid level position of the fluid medium in the lower annular space 11 exceeds ⅔ of the height of the artificial formation 4 and is not higher than the height of the upper support ring 12, at this time a liquid level height H00 of the fluid medium in the lower annular space 11 at the initial time is recorded;

a step S6 of injecting the fluid medium that is the same as that in the lower annular space 11 between the outer cylinder 1 and the air cushion 5 into the artificial borehole 41 of the artificial formation 4 through the liquid injection pipe 22, until the pressure value monitored by the pressure sensor 32 located within the artificial borehole 41 reaches the set value W1;

a step S7 of maintaining a pump pressure of the water pump for a set time period, and meanwhile monitoring and recording data of the liquid level height of the fluid medium in the lower annular space 11 in real time by the liquid level monitor 31 until the liquid level height H0 is stable after monitoring for a certain period of time;

a step S8 of reducing the pressure of the water pump and recording the pressure data of the pressure sensor 32 until reaching the set pressure N1 and maintaining it for a certain period of time, and monitoring the liquid level height H1 of the fluid medium in the corresponding lower annular space 11;

a step S9 of referring to the steps S7-S8, continuing to reduce the pressure of the fluid medium within the artificial borehole 41 to the set values N2, N3, . . . , until the pressure decreases to a hydrostatic column pressure value, monitoring the liquid level height H2, H3, . . . , of the fluid medium in the corresponding lower annular space 11;

a step S10 of referring to the steps S5-S9, pressurizing the pressure of the fluid medium within the artificial borehole 41 to W2, W3, . . . , and observing the liquid level height of the fluid medium in the corresponding lower annular space 11 and the liquid level height of the fluid medium in the corresponding lower annular space 11 after depressurization.

The formation respiration effect simulation device provided by the present invention is simple in structure and convenient in use, can simulate the process of formation respiration effect under different formation conditions and different operation conditions by setting different experimental conditions, and explore a solution to reduce the disadvantage of formation respiration effect on recognition of drilling conditions.

The formation respiration effect simulation device provided by the present invention can truly simulate the actual working conditions of the field and carry out the indoor simulation of the formation respiration effect; and can simulate the process that fluid within the artificial borehole enters the artificial formation under different pressure and the quantity of that fluid entering the artificial formation; and can further stimulate the process that the fluid medium that enters the artificial formation returns into the artificial borehole and the quantity of the returned fluid medium; the invention can solve the problem that the formation respiration effect is difficult to recognize during on-site operation, which leads to complex downhole accidents caused by blind well control operation.

Embodiment 2

As shown in FIGS. 1 to 3, the present invention also provides a simulation method of the formation respiration effect simulation device as described above, the simulation method comprising the steps of:

a step S1 of injecting a fluid medium into the lower annular space 11 of the formation respiration effect simulation device, and recording an initial liquid level height in the lower annular space 11;

a step S2 of injecting the fluid medium into an artificial borehole 41 of an artificial formation 4 through a liquid injection pipe 22 of the formation respiration effect simulation device, and monitoring pressure data in the artificial borehole 41 by a pressure sensor 32, until a pressure value monitored by the pressure sensor 32 reaches an initial set pressure value;

a step S3 of maintaining the initial set pressure value for a set time period, and monitoring a liquid level height of the fluid medium in the lower annular space 11 by the liquid level monitor 31;

a step S4 of changing the injection pressure of the fluid medium flowing into the liquid injection pipe 22 and maintaining the injection pressure for a certain period of time, and monitoring the current liquid level height of the fluid medium in the lower annular space 11 in real time by the liquid level monitor 31.

The simulation method provided by the present invention is implemented using the formation respiration effect simulation device described in Embodiment 1. The specific structure, working principle and beneficial effects of the formation respiration effect simulation device have been specifically described in Embodiment 1, and will not be repeated here. The simulation method can simulate the process that fluid within the artificial borehole enters the artificial formation under different pressure and the quantity of that fluid entering the artificial formation; and can further stimulate the process that the fluid medium that enters the artificial formation returns into the artificial borehole and the quantity of the returned fluid medium, this simulation method can truly simulate the actual working conditions of the field and carry out the indoor simulation of the formation respiration effect.

The simulation method can simulate the process of formation respiration effect under different formation conditions and different operation conditions by setting different experimental conditions, and explore a solution to reduce the disadvantage of formation respiration effect on recognition of drilling conditions.

The foregoing are several embodiments of the present invention, and those skilled in the art may make various modifications or variations to the embodiments of the present invention according to the disclosure of the application documents without departing from the spirit and scope of the present invention.

The invention claimed is:

1. A formation respiration effect simulation device, comprising:
   an outer cylinder in which an artificial formation is disposed, the artificial formation having an artificial borehole, an outer portion of the artificial formation being wrapped by an air cushion, and a lower annular space being formed between the air cushion and the outer cylinder;
   an inner cylinder which is hermetically disposed above the artificial formation, an upper annular space being formed between the inner cylinder and the outer cylinder, the upper annular space communicating with the lower annular space; a liquid injection pipe being pierced in the inner cylinder, and the liquid injection pipe being able to extend into the artificial borehole; and
   a monitoring mechanism having a liquid level monitor capable of monitoring a liquid level height of a fluid medium in the lower annular space, and a pressure sensor disposed at a lower end surface of the inner cylinder and located within the artificial borehole.

2. The formation respiration effect simulation device according to claim 1, wherein the lower annular space is provided with at least two support rings, which sleeve on an outer side of the air cushion and are spaced apart in an axial direction of the outer cylinder, and each support ring is provided with a plurality of flow grooves at intervals in a circumferential direction thereof.

3. The formation respiration effect simulation device according to claim 1, wherein the liquid level monitor is an infrared ranging sensor which is disposed at an upper end of the outer cylinder; or the liquid level monitor is a graduation line provided on an upper outer wall of the outer cylinder.

4. The formation respiration effect simulation device according to claim 1, wherein a liquid injection valve is provided at an upper end of the outer cylinder, and a liquid discharge valve is provided at an lower end of the outer cylinder, the liquid injection valve communicates with the upper annular space, and the liquid discharge valve communicates with the lower annular space.

5. The formation respiration effect simulation device according to claim 1, wherein the outer cylinder is a transparent cylinder, and an outer portion of the outer cylinder is wrapped by a metal protective layer.

6. The formation respiration effect simulation device according to claim 1, wherein an outer wall of a lower end of the inner cylinder is provided with a ring boss having an outer diameter that is the same as an outer diameter of the air cushion.

7. The formation respiration effect simulation device according to claim 1, wherein the inner cylinder has an inner cylinder body, a lower end of the inner cylinder body is hermetically connected with an inner sealing cover, and an upper end of the inner cylinder body is hermetically connected with an upper cover, the liquid injection pipe passes through the upper cover and the inner sealing cover, and the liquid injection pipe is in sealed connection with the inner sealing cover.

8. The formation respiration effect simulation device according to claim 7, wherein a plurality of axial through grooves are provided at intervals in a circumferential direction on an inner wall of the inner cylinder body, and a plurality of sliding blocks are provided at intervals in a circumferential direction on an outer wall of the inner sealing cover, and the sliding blocks are embedded in the axial through grooves in a sealed sliding manner.

9. The formation respiration effect simulation device according to claim 8, wherein a plurality of insertion blocks are provided at intervals in a circumferential direction on a lower end face of the upper cover, and in a state that the upper cover is placed on the upper end of the inner cylinder body, the insertion blocks can be clamped in the axial through grooves.

10. A simulation method using the formation respiration effect simulation device according to claim 1, the simulation method comprises the following steps:
   a step S1 of injecting a fluid medium into the lower annular space of the formation respiration effect simulation device, and recording an initial liquid level height in the lower annular space;
   a step S2 of injecting the fluid medium into the artificial borehole of the artificial formation through the liquid injection pipe of the formation respiration effect simulation device, and monitoring pressure data in the artificial hole by the pressure sensor, until a pressure value monitored by the pressure sensor reaches an initial set pressure value;
   a step S3 of maintaining the initial set pressure value for a set time period, and monitoring a liquid level height of the fluid medium in the lower annular space by the liquid level monitor; and
   a step S4 of changing an injection pressure of the fluid medium flowing into the liquid injection pipe and maintaining the injection pressure for a certain period of time, and monitoring the current liquid level height of the fluid medium in the lower annular space in real time by the liquid level monitor.

* * * * *